United States Patent [19]
Gustafson et al.

[11] Patent Number: 4,876,208
[45] Date of Patent: Oct. 24, 1989

[54] DIFFRACTION IMMUNOASSAY APPARATUS AND METHOD

[75] Inventors: Eric K. Gustafson, Palo Alto; Rick Trebino, Livermore; John Lee, Cupertino, all of Calif.

[73] Assignee: Yellowstone Diagnostics Corporation, Sunnyvale, Calif.

[21] Appl. No.: 9,177

[22] Filed: Jan. 30, 1987

[51] Int. Cl.$^4$ .......................................... G01N 33/545
[52] U.S. Cl. ...................................... 436/531; 422/58; 436/164; 436/805
[58] Field of Search ........................ 436/531, 805, 164; 422/58

[56] References Cited

U.S. PATENT DOCUMENTS 4,521,522  6/1985  Lundström ................... 436/531 X
4,537,861  8/1985  Elings ............................ 436/805 X
4,647,544  3/1987  Nicoli ............................ 436/531 X

FOREIGN PATENT DOCUMENTS

WO86/901  3/1986  PCT Int'l Appl. .

Primary Examiner—Barry S. Richman
Assistant Examiner—Jill Johnston
Attorney, Agent, or Firm—William B. Walker

[57] ABSTRACT

A diffraction immunoassay method in which a diffraction grating design of non-light disturbing primary binding reagent on an insoluble surface is conjugated with analyte in a sample. If the primary binding reagent-analyte conjugate is light disturbing, a diffraction grating is formed. If the primary binding reagent-analyte conjugate is non-light disturbing, the analyte is further conjugated with a secondary binding reagent which is labeled with a light disturbing material to form a diffraction grating. Light from a narrow band light source is then applied to the surface, and the intensity of beams of diffracted light formed by the diffraction grating is determined. The diffraction immunoassay plate for the method comprises a smooth insoluble surface having on the surface thereof, a diffraction grating design of lines of the primary binding reagent. The diffraction immunoassay apparatus comprises a light source, a platform for supporting the diffraction immunoassay plates in the path of a beam of light from the light source, and at least one light detector positioned to detect light diffracted by the diffraction grating.

9 Claims, 3 Drawing Sheets

DIFFRACTION IMMUNOASSAY APPARATUS AND METHOD

FIELD OF THE INVENTION

This invention relates to a novel immunoassay system and method, and the apparatus and reagents therefor. In particular this invention relates to an immunoassay apparatus and method for determining the presence and amount of an analyte in a sample using a light diffraction grating, a light source and a light detector which measures the light diffracted by the grating.

BACKGROUND OF THE INVENTION

Many solid-phase immunoassays involve surface illumination and consequent light emissions from molecules attached to the surface. Generally, these emissions travel in all directions. Either these divergent emissions must be collected with expensive and awkward light collection optics to achieve sensitivity or the inherent inefficiencies and consequent low signal to light level ratios must be accepted.

Diffraction gratings have been used for dispersing light into its spectral components. The original gratings were prepared by ruling a number of straight, parallel grooves in a surface. Incident light is diffracted by each of the surfaces and is principally directed in directions in which light from each groove interferes constructively with light scattered by the other grooves.

Many immunoassay systems have been developed using different physically measurable properties of reagents to provide a measurement of an analyte concentration in a sample. Radio immunoassay (RIA), immunofluorescence, chemiluminescence, enzyme immunoassays (EIA), free radical immunoassays (FRAT), light scattering nephelometry, transistor bridge probes, indium reflective surfaces, and ultrasonic probes have been applied. These systems use the highly selective reaction between a primary binding reagent material such as an antibody or antigen and an analyte selectively binding therewith.

DESCRIPTION OF THE PRIOR ART

An attempt by others to develop an optical probe comprising a metal covered diffraction grating coated with a monoclonal antibody specific for a virus, bacterium or other desired antigen has been described by Moffatt, A. *Genetic Engineering News*. p 18, October 1986. The shift in wavelength of reflected light is apparently determined and correlated to a concentration in analyte. Moffatt says the manufacture of the grating in commercial quantities has not been achieved because he lacks a suitable method for mass production of quality gratings.

A reflectance method for quantification of immunological reactions on polished crystalline silicon wafer surfaces has been described by Arwin, H. et al, *Analytical Biochemistry*. 154:106–112 (1985). Indium surface reflection methods are described by Giaever in U.S. Pat. Nos. 3,853,467, 3,926,564, 3,960,488, 3,960,489, 3,960,490, 3,975,238, 3,979,184, 3,979,509, 4,011,308, 4,018,886, 4,054,646, 4,115,535, 4,172,827 and 4,181,501. Liquid layer thicknesses can be monitored by a reflectance method described in U.S. Pat. No. 3,960,451.

Biosensors such as field effect transistors probes and their use in assays are described by Pace, S., *Medical Instrumentation*. 19(4):168–172 (1985). Polysilicon surfaces are included among the possible biosensor surfaces to which primary binding reagents can be attached.

Photoresists and laser light have been used to make holographic gratings. The coarseness of the photographic medium restricts the groove spacing. Use of photoresist masks in the production of precisely configured shapes and lines in semiconductor material is widely used in the production of semiconductor devices. However, these procedures have not been previously used to manufacture diffraction gratings of metal or of grating lines of primary binding reagent on an insoluble surface.

SUMMARY OF THE INVENTION

The apparatus of this invention comprises the combination of a light source, a platform means for supporting an insoluble surface having a diffraction grating on the surface thereof in the path of light from the light source, and a light detector positioned to detect light diffracted by the diffraction grating. The light source is preferably a narrow band light source, optimally providing collimated, intense, polarized light. The insoluble surface has a diffraction grating pattern or design of substantially non-light disturbing primary binding reagent thereon. The design does not diffract significant light unless and until it is coupled through the primary binding reagent with a light disturbing material.

An article of this invention is the insoluble surface with the light diffracting design of substantially non-light disturbing primary binding reagent, and the light diffracting product thereof which is formed when a light-disturbing material is coupled to the insoluble surface through the primary binding reagent. In an optimum embodiment, the insoluble surface to which the lines of primary binding reagent are adhered is a polysilicon surface.

The immunoassay method of this invention comprises contacting a diffraction grating design of non-light disturbing binding reagent on an insoluble surface with a sample for a time sufficient to permit conjugation of primary binding reagent and analyte in the sample. The sample is then removed from the insoluble support, the surface is illuminated with light from a light source, and the diffraction of light by the insoluble surface is determined. In a preferred embodiment of the method of this invention, the light source is a source of narrow band light, and optimally an intense, polarized, collimated light. If the product produced in the conjugation of primary binding reagent and analyte is non-light disturbing, the insoluble support having primary binding reagent conjugated with analyte thereon can be conjugated with a solution of secondary binding reagent which is labeled with a light-disturbing material to produce a diffraction grating on the insoluble support.

DETAILED DESCRIPTION OF THE INVENTION

This invention is based on a novel application of light diffraction. By forming a grating of binding reagent-analyte complexes on the surface of an insoluble support, the incident light can be diffracted into a discrete series of angles, and the light can be detected and measured with a high efficiency. The angle of diffraction is a function of the grating line spacing and the wavelength of the incident light.

The term "binding reagent" is used herein to designate one member of a binding pair of compounds or materials which selectively bind to form a conjugate. The term "primary binding reagent" is used herein to designate the non-light disturbing binding reagent which is applied to the insoluble surface to form a diffraction grating design of non-light disturbing material.

The term "immunoassay", as used herein, is used to designate an assay using any binding reaction between a binding reagent and the other member of the binding pair which is selectively bindable therewith. The selective binding can be provided by the well-known interaction of an antibody with an antigen or hapten epitope with which it selectively binds. Other examples of immunoassay binding pairs are biotin-avidin, lectin-sugar, IgG antibody Fc portion with protein A, and the like. In general, the primary binding reagent is selected to bind specifically or selectively with the analyte, the material for which a sample is assayed.

The term "light disturbing", as used herein, is defined to include all ways in which light is affected including light absorbing, reflecting, scattering, refracting and phase changing.

The term "diffraction grating", as used herein, is defined to include reflection amplitude gratings which are formed in one or more immunological steps. In one step gratings, the diffraction grating is formed directly by the conjugation of the non-light disturbing reagent on the insoluble surface with a light disturbing analyte. In multistep gratings, the conjugation product of the non-light disturbing reagent on the insoluble surface with the analyte is non-light disturbing. By conjugation of the analyte with a light disturbing material in one or more further conjugations, a multistep grating is formed. Types of single and multistep gratings formed in the process of this invention include reflection amplitude gratings, transmission amplitude gratings, reflection phase gratings, and transmission phase gratings. In reflection amplitude gratings in one or more steps, light is reflected from the grating, and the amplitude of the reflected light is modulated by the spatially variable reflection of the grating. In transmission amplitude gratings in one or more steps, light is transmitted through the grating, and the amplitude of the transmitted light is modulated by the spatially variable transmission of the grating. In the reflection phase grating in one or more steps, the light is reflected from the grating, and the phase of the reflected light is modulated by the spatially variable refractive index of the grating. In the transmission phase gratings in one or more steps, light is transmitted through the grating, and the phase of the transmitted light is modulated by the spatially variable refractive index of the grating. In the method of this invention, the diffraction grating may function as one or more of these types of gratings concurrently, and all of these grating types are included within the diffraction gratings of this invention.

Figure 1:
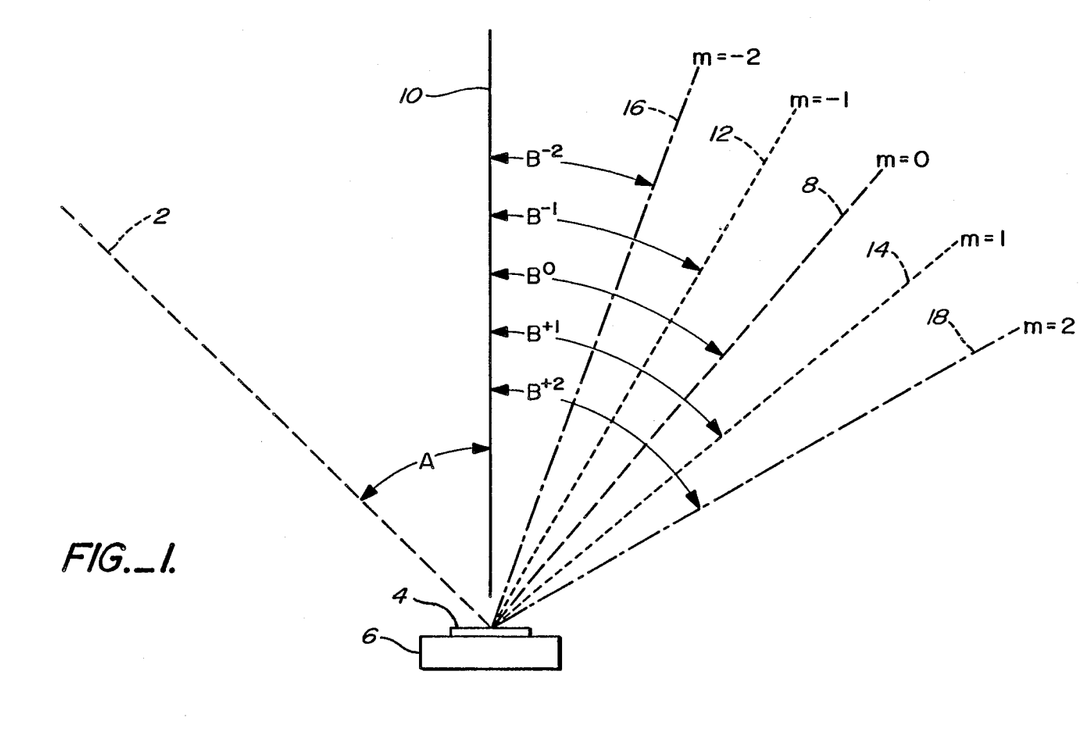
FIG. 1 is a schematic of incident and diffracted light designs in the method of this invention.

FIG. 1 is a schematic of incident and diffracted light designs produced by incident light impinging on the diffraction grating in the method of this invention. The incident light 2 impinges on a diffraction grating 4 on the surface of the insoluble support 6. Reflected light 8 (m=0) is reflected at angle $B^0$ which is equal to angle A, the angle of incidence, measured with respect to the normal 10 to the grating surface 4. Diffracted light is diffracted by the grating 4 in a series of angles. The relationship between the angle of incident and the angle of diffraction is provided by the basic grating equation:

$$mL = d(\sin A - \sin B)$$

wherein m is the spectral order of wavelength lambda (herein represented by "L"), d the groove spacing, and A and B are the angles of incidence and diffraction, respectively, with respect to the normal to the grating surface. The first order diffractions 12 (m=−1) and 14 (m=1) have angles $B^{-1}$ and $B^{+1}$. The second order diffractions 16 (m=−2) and 18 (m=2) have angles $B^{-2}$ and $B^{+2}$ with respect to normal 10. Light is also diffracted at higher orders. The first and second order diffractions are shown by way of example, not as a limitation, and all diffractions having a significant intensity can be used in the method of this invention.

Figure 2:
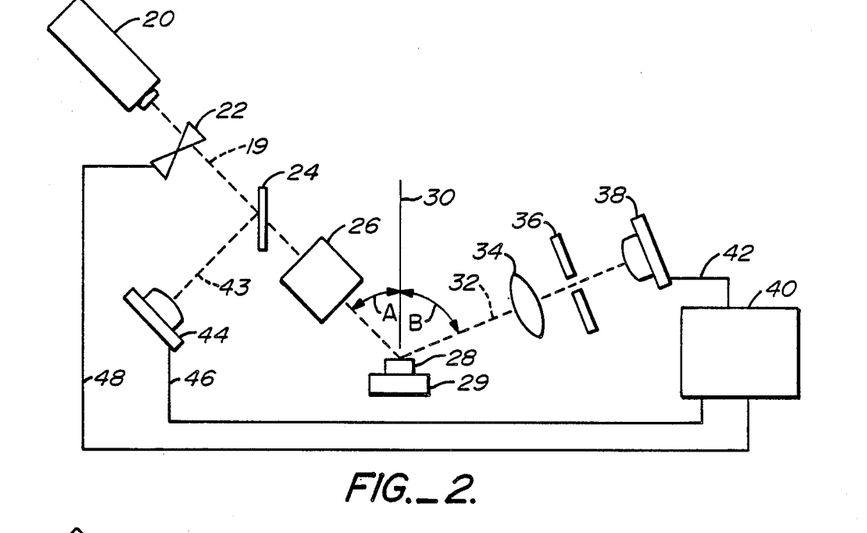
FIG. 2 is a schematic view of a stationary platform embodiment of the diffraction immunoassay apparatus of this invention.

FIG. 2 is a schematic view of a stationary platform embodiment of the diffraction immunoassay apparatus of this invention. The light beam 19 from the light source 20 passes through chopper 22 and beam splitter 24. The light passing the splitter passes through collimator 26 and impinges on the diffraction grating 28 mounted on the stationary support 29.

A diffracted beam leaving the grating surface 28 is represented by single line 32 having an angle B with respect to the normal 30. The reflected beam is not shown. The light is collected with lens 34, is passed through an aperture 36 and impinges on the light sensor 38, generating an electrical signal which is carried to the conventional lock-in amplifier and recorder system 40 by cable 42. A split beam 43 of light diverted by the splitter 24 from the primary beam 19 is directed against another light detector 44. The electrical signal from the light detector 44 is fed by cable 46 to the lock-in amplifier 40 as a reference signal for compensating slow drift errors originating from the light source. Cable 48 provides a reference signal from the chopper 22 to the lock-in amplifier 40 for the lock-in function. This function synchronizes the chopper speed (the light bundles passing the chopper) with the operation (opening) of the amplifier filter, thus reducing ambient light noise. The components of the system and their individual functions including the light source, splitter, chopper, collimator, lens, light detectors and lock-in amplifier are conventional and well-known in the art.

The diffraction measuring apparatus schematically represented in FIG. 2 can be constructed to change the angles A and B. The light source 20, chopper 22, beam splitter 24 and collimator 26 can be mounted on an arm which mounted to rotate in a vertical plane around the diffraction grating 28 to a preferred angle A. Angle A is preferably within the range of from 10° to 80° and optimally within the range of from 20° to 70°. Even more importantly, the lens 34, aperture 36 and light detector 38 can be mounted on an arm for rotation in a vertical place around the diffraction grating 28 through angles B which place the lens and aperture in the paths of the reflected light beam 8 and the diffracted light beams represented by 12, 14, 16 and 18 in FIG. 1. In this manner, a single detector system can be rotated to detect and measure the reflected light and all desired orders of the diffracted light.

Figure 3:
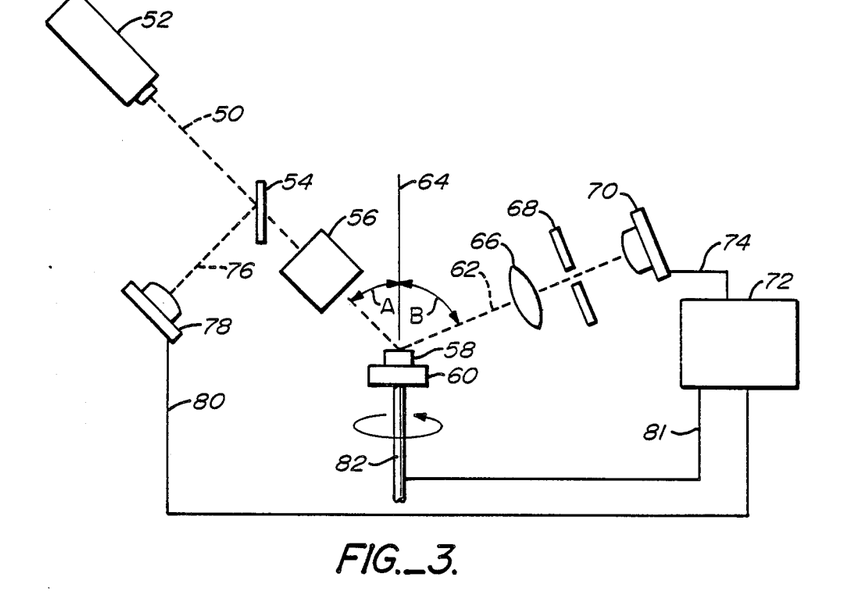
FIG. 3 is a schematic view of a rotating platform embodiment of the diffraction immunoassay apparatus of this invention.

FIG. 3 is a schematic view of a rotating platform embodiment of the diffraction immunoassay apparatus of this invention. The light beam 50 from the light source 52 passes through the beam splitter 54. The light passing the splitter passes through collimator 56 and impinges on the diffraction grating 58 mounted on the rotating support 60.

The diffracted light beam 62 leaving the grating surface 58 has an angle B with respect to the normal 64 to the grating surface. The light is collected with lens 66, is passed through an aperture 68 and impinges on the light sensor 70, generating an electrical signal which is carried to the conventional lock-in amplifier and recorder system 72 by cable 74. A split beam 76 of light diverted by the splitter 54 from the primary beam 50 is directed against another light detector 78. The electrical signal from the light detector 78 is fed by cable 80 to the lock-in amplifier 72 as a reference signal for compensating slow drift errors originating from the light source 52. Cable 80 provides a signal from the platform rotating system 82 to the lock-in amplifier 72 for the lock-in function. This function synchronizes the platform speed (the periodic alignment of the grating and light diffraction designs therefrom with the lens 66 and aperture 68) with the operation (opening) of the amplifier filter, thus reducing ambient 15 light noise. The components of the system and their individual functions including the light source, splitter, light detectors and lock-in amplifier are conventional and well-known in the art.

The diffraction measuring apparatus schematically represented in FIG. 3 can also be constructed to change the angles A and B. The light source 52, beam splitter 54 and collimator 56 can be mounted on an arm which mounted to rotate in a vertical plane around the diffraction grating 58 to a preferred angle A. Angle A is preferably within the range of from 10° to 80° and optimally within the range of from 20° to 70°. Even more importantly, the lens 66, aperture 68 and light detector 70 can be mounted on an arm for rotation in a vertical place around the diffraction grating 58 through angles B which place the lens and aperture in the paths of the reflected light beam 8 and the diffracted light beams represented by 12, 14, 16 and 18 in FIG. 1. As in the embodiment shown in FIG. 2, a single detector system can be rotated to detect and measure the reflected light and all desired orders of the diffracted light.

Alternatively, a stationary array of lens, aperture and detector sets can be positioned at preset angles to coincide with the pats of the reflected and diffracted light for both of the systems of FIG. 2 and FIG. 3. For most simple embodiments of these systems, a stationary lens, aperture and light detector set can be positioned in the path of a first, second or third order diffracted beam. Other suitable combinations of stationary and movable arrays of detectors will be apparent to a person skilled in the art, and all of these permutations and combinations are intended to be within this invention.

The light sources 20 (FIG. 2) and 52 (FIG. 3) are preferably narrow band light sources which can include filtered light from an incandescent light bulb or sun light. The most preferred light is intense narrow band light which is collimated and optimally polarized. The narrow band frequency can be within the range of from 200 to 1400 nm having a band width within the range of from 10 to 80 nm and is optimally within the range of from 400 to 800 nm having a band width of from 10 to 20 nm or lower. The output power or output energy level of the light source can be 0.1 milliwatts and higher, the higher the power level, the better the results.

The optimum light sources are monochromatic light sources such as lasers. Optimum monochromatic light sources are lasers such as helium-neon laser, diode laser, diode pumped solid state laser, argon ion laser, helium-cadmium laser, YAG, harmonics of YAG, ruby, excimer and tunable dye lasers. The light can be polarized or not polarized. Linear polarization in the plane of incidence is optimum.

The light chopper 22 (FIG. 2) can be any conventional light chopper. It can comprise a rotating plate defining evenly radially spaced windows at a constant distance from the axis of rotation of the plate.

A beam expander can be optionally provided in the light paths 19 and 50 to increase the cross-sectional area of the beams and increase the surface area of the diffraction grating interacting with the light to increase sensitivity. Preferred beam expanders are conventional lens or prism systems which convert an incident collimated light beam into an emitted collimated beam of larger size.

The collecting lenses 34 (FIG. 2) and 66 (FIG. 3) collect each of the diffracted light beams and concentrate or focus them into smaller beams having a cross-sectional area less than the surface area of the light detectors 38 and 70. Any conventional lens system can be used which provides the desired reduction or focusing.

The light detectors 38 and 70 can be any devices which can quantitatively convert incident light intensity to voltage or current in a proportional manner. Conventional light detectors such as photomultiplier tubes or semiconductor-based detectors such as silicon, germanium or gallium arsenide can be used.

The amplifier and recorder systems 40 and 72 can be any conventional system which is customarily used for amplifying an input signal from a light detector and recording a value functionally related thereto. A simple system can comprise a bias supply and an oscilloscope adjusted to show the amplitude of the output signal of each light detector 38 and 70. For more sensitivity, a lock-in amplifier which uses a reference signal from the chopper (FIG. 2) or rotating mount (FIG. 3) to perform the functions described above. These amplifiers are standard, commercially available systems fully within the existing skill of the art and are not a part of this invention.

The platform 6 (FIG. 1) is designed to support a diffraction grating in a precise position of alignment with the incident light beam 2. The configuration of the platform 6 is determined by the shape of the diffraction surface support and whether more than one diffraction surface is mounted on a diffraction surface support.

Figure 4:
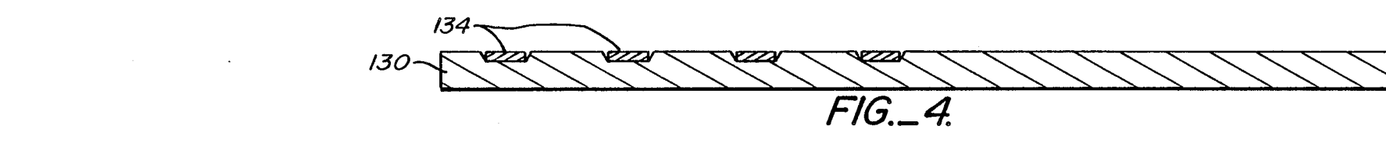
FIG. 4 is a cross-sectional view of a dipstick having mounted thereon, a plurality of insoluble supports with diffraction grating designs of reagents on the surfaces thereof.

FIG. 4 is a cross-sectional view of a dipstick having mounted thereon, a plurality of insoluble supports with non-light disturbing diffraction grating designs of reagents on the surfaces thereof. The dipstick body 130 has a plurality of insoluble support surfaces 134 having a diffraction grating design of binding reagent coated thereon. The materials from which the dipstick is made should be non-binding to minimize non-specific binding during the immunoassay procedure. Suitable dipstick surface materials include polyolefins such as polyethylene and polypropylene, hydrophilic polysilicon and polysiloxane polymers, and the like. Also suitable are polymers which have been treated to render the surfaces non-binding to proteinaceous materials.

The support for the diffraction grating supports can be any articles upon which the diffraction grating support surface can be mounted. The description of dipsticks are provided by way of example, and not as a limitation. Other articles such as microwells, plates, cavities and the like can be used. For many applications, dipsticks are a preferred embodiment.

Figure 5:
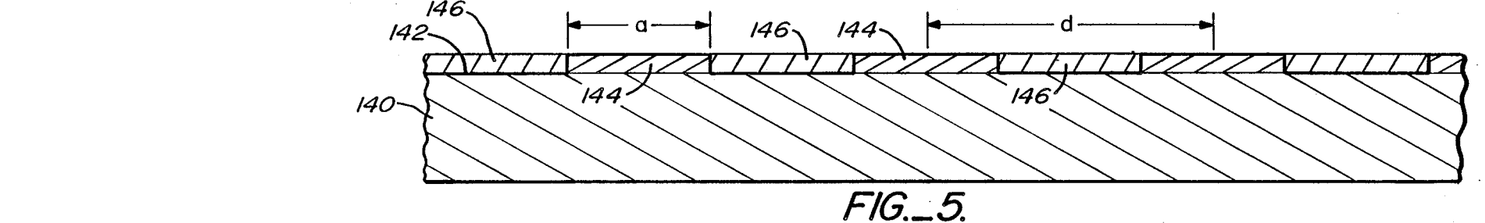
FIG. 5 is a fragmentary, magnified cross-sectional view of an insoluble support having primary binding reagent on the surface thereon in a diffraction grating design.

FIG. 5 shows one embodiment of a diffraction grating element of this invention. FIG. 5 is a fragmentary, magnified cross-sectional view of an insoluble support having primary binding reagent on the smooth surface thereof in a non-light disturbing diffraction grating design. The insoluble support 140 of this embodiment has a smooth upper surface 142 upon which the diffraction grid design or pattern is coated. The diffraction grating design comprises a plurality of lines 144 of non-light disturbing active primary binding reagent thinly coated and adhering to the upper surface 142. The lines 144 are separated by lines 146 of deactivated primary binding reagent, for example, primary binding reagent which has been deactivated by exposure to ultraviolet (UV) radiation, other deactivating radiation or other deactivation energy.

The grating can have any number of lines 144 which will provide a diffraction design with the incident light wavelength. The preferred density of lines 144 are from 250 to 10,000 lines per cm for polarized monochromatic light having a wavelength of from 600 to 800 nm. The optimum density of lines 144 is from 1250 to 2500 lines per cm for polarized monochromatic light having a wavelength of from 600 to 850 nm. The lines 144 have a preferred width (a) of from 0.5 to 20 microns and an optimum width of from 2 to 8 microns. The spacing "d" between the center of adjacent lines 144 is preferably from 0.5 to 20 microns and optimally from 1 to 12 microns. The lines 144 and 146 can be of any desired thickness, depending upon the nature of the primary binding reagent. For antibody and antigen coatings adhered to the surface 142 by adsorption or other bonding procedures, the coating thickness is preferably a thin coating, yielding a layer which is non-light disturbing. Prior to the conjugation of the coating 144 with a non-light disturbing substance, the grating is non-diffracting, that is, no diffraction occurs when it is exposed to light. When the coating 144 is conjugated with a light disturbing substance, the grating becomes a diffracting grating. The proportion of light diffracted is a function of the concentration or quantity of light disturbing materials conjugated with the coating 144, and this value can be used to verify the presence of analyte and to quantify the concentration of analyte present in a sample.

The smooth upper surface 142 can be any material to which a primary binding reagent can be adhered by physical or chemical bonding and which will not interfere with the reactions which are used to determine the presence and extent of the conjugating reaction. Organic and inorganic polymers, both natural and synthetic, can be used as the insoluble support. Examples of suitable polymers include polyethylene, polypropylene, polybutylene, poly(4-methylbutylene), butyl rubber, silastic polymers, polyesters, polyamides, cellulose and cellulose derivatives (such as cellulose acetate, nitrocellulose and the like), acrylates, methacrylates, vinyl polymers (such as polyvinyl acetate, polyvinyl chloride, polyvinylidene chloride, polyvinyl fluoride, and the like), polystyrene and styrene graft copolymers, rayon, nylon, polyvinylbutyrate, polyformaldehyde, etc. Other materials which can be used as the insoluble support can be silicon wafers, glass, insoluble protein coatings on a smooth insoluble surface, metals, metalloids, metal oxides, magnetic materials, materials used in semiconductor devices, cements and the like.

The preferred diagnostic supports of this invention have a superior adsorptive quality for physical, non-covalent binding of proteins, including primary binding reagents and proteinaceous materials applied to reduce the non-specific binding of the ultimate coating. We have discovered that materials previously used in the manufacture of semiconductor devices have superior qualities in this respect. Suitable materials include polished single crystalline aluminum, silicon, epitaxial silicon coatings, silicon nitride coatings, silicon dioxide coatings, and polysilicon coatings. The optimum surfaces have a polysilicon coating. The most optimum supports 140 are single crystal silicon wafers having a polysilicon coating on the outer polished surface thereof.

The polysilicon surface is preferably a thin film of polysilicon deposited on a suitable surface, preferably a highly polished surface such as a single crystalline silicon wafer. Polysilicon films were developed in the semiconductor industry as valuable dielectric materials. They are used as gate electrodes in MOS devices, for high value resistors, diffusion sources to form shallow junctions, conductors and to ensure ohmic contact to crystalline silicon. The term "polysilicon" as used herein is synonymous with the term "polycrystalline silicon". These films are conventionally prepared by chemical vapor deposition techniques. These films and method for their preparation are described by A. C. Adams in "Dielectric and Polysilicon Film Deposition", VLSI TECHNOLOGY. (S. M. Sze ed.) New York: McGraw-Hill, pp 93–129 (1983) and the citations therein, the entire contents of which are hereby incorporated by reference. The surface upon which the polysilicon is coated can be any material which is stable at polysilicon deposition temperatures. It can be prepared by pyrolyzing silane at 600° to 650° C. in a partial vacuum. Lower pyrolysis temperatures are suitable with more reactive silicon sources such as disilane.

The primary binding reagent can be bound to the insoluble support by adsorption, ionic bonding, van der Waals adsorption, electrostatic bonding, or other non-covalent bonding, or it can be bound to the insoluble support by covalent bonding. Procedures for non-covalent bonding are described in U.S. Pat. No. 4,528,267. Procedures for covalently bonding antibodies and antigens to insoluble supports are described by Ichiro Chibata in IMMOBILIZED ENZYMES. Halsted Press: New York (1978) and A. Cuatrecasas, *J. Bio. Chem.* 245:3059 (1970), the entire contents of which are hereby incorporated by reference. The surface can be coated with a protein and coupled with the primary binding reagent using procedures described in U.S. Pat. No. 4,210,418 using glutaraldehyde as a coupling agent, for example. In another procedure, the insoluble support can be coated with a layer having free isocyanate groups such as a polyether isocyanate, and application of the antibody or antigen in aqueous solution thereto effects the requisite bonding. In further procedure, the antibody or antigen can be coupled to a hydroxylated material by means of cyanogen bromide as described in U.S. Pat. No. 3,720,760.

Figure 6:
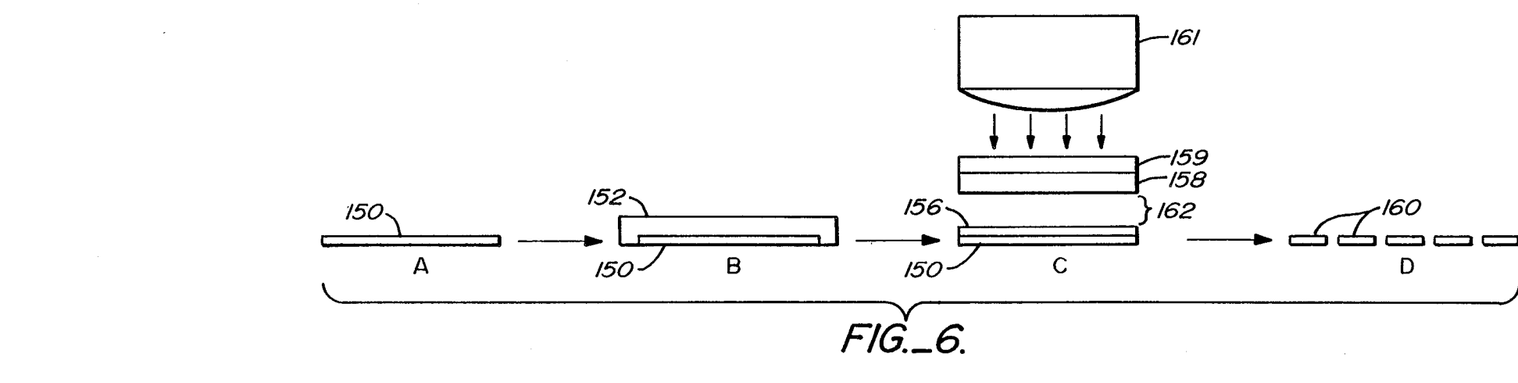
FIG. 6 is a schematic representation of the process for manufacturing an insoluble support with the diffraction grating design of FIG. 5.

FIG. 6 is a schematic representation of a process for preparing the insoluble support with a diffraction grating design of primary binding reagent shown in FIG. 5. Any smooth surface having the requisite high binding affinity for primary binding reagent can be used in this process. For purposes of clear explanation and not by way of limitation, the process is described for a semiconductor wafer with a polished surface bearing a polysilicon coating. It should be understood that the same, equivalent, or similar procedures can be applied for preparing diffraction gratings designs with primary binding reagents with other high binding smooth surfaces.

With the preferred insoluble supports of aluminum, silicon nitride, silicon dioxide, single crystalline silicon, and particular the polysilicon surfaces, the primary binding reagent can be applied by simple adsorption. In one procedure for non-covalent adhesion of primary binding reagent to the surface of an insoluble support, a primary binding reagent such as an antibody, antigen or hapten-protein conjugate is applied to the surface of a support such as a polysilicon surface 150 (Step A) in an aqueous buffer solution 152 in Step B. The buffered primary binding reagent solution is placed in a container with the support bearing the polysilicon surface and incubated at room temperature until adsorption occurs, for example for from 0.5 to 18 hours and preferable from 1 to 3 hours, at temperatures of from 4° to 40° C. and preferable from 20° to 26° C. The polysilicon surface is then rinsed with a buffered saline solution and dried.

The concentration of primary binding reagent in the buffer solution is selected to provide the desired reagent density on the polysilicon surface. The primary binding reagent solution can contain from 0.02 to 100 micrograms/ml of the primary binding reagent and preferably contains from 10 to 50 micrograms/ml of the primary binding reagent in a buffered solution having a pH of from 6.0 to 9.5 and preferably from 7.0 to 8.5.

Primary binding reagents are chosen to bind selectively with the analyte to be measured in a sample. For example, the primary binding reagent can be a polyclonal antibody, a monoclonal antibody or a mixture of monoclonal antibodies binding specifically with a sample analyte to be measured. For determining antibodies binding with a specific antigen in a sample, the binding reagent can be an antigen binding with the analyte antibody, such as an allergen which binds with IgE antibody in a solution. The primary binding reagent can also be a hapten or antigen conjugated with a water-soluble protein or polymer which adheres more strongly or more uniformly to the polysilicon surface than the simple hapten or antigen. The primary binding reagent can be other binding reagents such as biotin for the analyte avidin, avidin for the analyte biotin, lectin, Protein A for antibodies binding therewith, and the like.

The surface 150 with the coating 156 thereon is then rinsed and dried.

A suitable rinse solution is an aqueous phosphate buffer solution such as is described in U.S. Pat. No. 4,528,267 having a phosphate polarity of from 0.0001 to 0.05, a pH of from 6 to 8 and containing from 0.001 to 0.1 weight percent non-ionic surfactant and from 0.0001 to 0.5 weight percent of an animal serum albumin. Suitable non-ionic surfactants include polyoxyethylene ethers (BRIJ) such as lauryl, cetyl, oleyl, stearyl, and tridecyl polyoxyethylene ethers; polyoxyethylenesorbitans (TWEEN) such as polyoxyethylenesorbitan monolaurate, monopalmitate, monostearate, monoleate and trioleates; and other polyoxyethylene ethers (TRITON), for example. Preferred non-ionic surfactant are the polyoxyethylenesorbitans such as polyoxyethylenesorbitan monolaurate (TWEEN 20).

A mask is prepared by photographic methods conventional in semiconductor manufacturing. For example, a mask having a plurality of diffraction gratings having the desired line density and line widths can be prepared on a quartz glass or other UV-transparent plate through a photoresist process similar to photography. The dark lines of the mask correspond to active primary binding reagent areas desired on the ultimate surface.

In Step C, the mask 158 is placed over the polysilicon surface 150 having a coating 156 of primary binding reagent, and the surface is exposed to ultraviolet radiation until the binding capability of the portions of the primary binding reagent exposed to the radiation are substantially reduced or preferably eliminated. To manufacture a precision grating design, the radiation should form a sharp image on the coated surface. Penumbrae should be minimized. The penumbra can be minimized if the space between the mask and the surface is eliminated with pressure. Alternatively, the ultraviolet light passing through the mask can be focused to a sharp image on the surface coating using conventional projection alignment techniques.

The ultraviolet radiation exposure required to deactivate coating exposed thereto depends upon the primary binding reagent. For antibody primary binding reagents, exposure times of from 30 sec to 30 min and preferably from 1 to 5 min is sufficient with a ultraviolet radiation having a wavelength such as 254 nm and a power of from 8 to 14 milliwatts per $cm^2$. Some adjustment in time of exposure and/or power may be necessary to deactivate the binding sites of other antibody binding agents.

To alter the epitopes of antigenic primary binding reagents such as human IgG, exposure times of from 30 to 120 min and preferably from 45 to 60 min are sufficient with a ultraviolet radiation having a wavelength of 254 nm and a power of from 8 to 14 milliwatts per $cm^2$. Some adjustment in time of exposure and/or power may be necessary to alter or destroy the binding sites of other binding agents.

This treatment reduces or eliminates the binding properties of the primary binding reagent in lines 146, leaving active primary binding reagent in a diffraction grating design as the lines 144 of FIG. 5.

The coated substrate containing areas having binding protein in a diffraction grating design is then cut into smaller area chips 160 in Step D, each chip having a size sufficient to perform an immunoassay. These chips are then mounted on a suitable diagnostic support such as the dipstick shown in FIG. 4.

The method of this invention comprises a first step of contacting the insoluble support with the biological diffraction grating design or pattern of binding agent thereon with the sample to be assayed for an analyte which binds specifically with the binding agent. The insoluble support is contacted with the sample for a time sufficient to permit conjugation of the binding agent and the analyte. The sample is then removed from the insoluble support, preferably with a suitable buffered rinse solution such as described hereinabove. This procedure leaves the diffraction grating design of binding agent coupled with the analyte.

If the binding agent-analyte conjugation product is non-light disturbing, the second step comprises conjugating the insoluble support with a secondary binding reagent which is labeled with one or more light disturbing substances which affect light by absorption, reflection, scattering, refraction or phase changing. Specific examples include chromophores and other light absorbing materials, and reflective and light transmitting beads and other light reflecting and scattering materials. Alternatively it can be coupled with a secondary binding reagent which can be specifically conjugated with a binding partner therefor which is labeled with a chromophore or light absorbing material. This alternative coupling can occur during or subsequent to the secondary binding reagent treatment in the second step.

The choice of secondary binding reagent is made depending upon the type of analyte being assayed. If the analyte is an IgG antibody, for example, the secondary binding reagent can be either an IgG specifically binding antibody or Protein A, suitably labeled with a light disturbing material. In general, the secondary binding reagent is an antibody of a selected class which binds specifically with the analyte, usually an IgG class antibody.

Suitable chromophore labels are any light absorbing pigment or dye which absorbs light of the wavelength produced by the light source. Coupling of the binding reagent-analyte conjugation product with such a chromophore converts the light diffracting design into a diffraction grating. Alternatively, the light absorbing label can be another type of light disturbing particle or reflective material such as colloidal gold or silver, or latex microspheres.

In the alternative embodiment, the secondary binding partner label is selected to bind specifically with a tertiary binding reagent which is labeled with a suitable light disturbing material. Examples of binding pairs for which either partner can be used as the secondary binding partner label are avidin-biotin, IgG antibody-Protein A, hapten-antihapten antibody, and the like. If the secondary binding reagent is an IgG antibody, for example, it can be unlabeled, since the Fc chain portion thereof is a binding partner for Protein A or anti-IgG antibodies.

Following conversion of the biological diffraction design to a diffraction grating, insoluble support is rinsed with distilled or deionized water. Then the strength of the light diffraction is measured with a suitable light diffraction instrument such as is illustrated in FIG. 1. The relative strengths of the light diffracted is a function of the amount of primary binding reagent-analyte conjugate comprising the grating. By repeating the above procedure with a prepared series of solutions containing a range of different known concentrations of analyte therein, a standard curve functionally related to the strength of the diffracted light is obtained. By comparing the reading obtained with the sample containing the analyte with the curve obtained with solutions containing known concentrations of the analyte, the concentration of analyte in the sample can be determined. Comparing the strengths of the first, second, third, etc. order diffractions with each other and with the strength of the reflected light directly provides an indication of the degree of conjugation with the grating binding agent.

In a competition immunoassay alternative method, the insoluble support with the biological diffraction grating design of binding agent thereon can be contacted with a mixture of the analyte sample and a reagent analyte labeled with a label which is light disturbing The amount of reagent analyte binding with the primary binding agent will be an inverse function of the amount of analyte in the sample. The density of the diffraction grating formed will therefor have a functional relationship with the concentration of analyte in the sample, and this difference can be detected in the strength of diffracted light.

This invention is further illustrated by the following specific but non-limiting examples. Unless otherwise specified, percents are provided as weight percents and temperature as degrees Centigrade. Examples which have been carried out in the laboratory are set forth in the past tense, and examples setting forth procedures which are constructively reduced to practice herein are set forth in the present tense.

EXAMPLE 1

Antibody Diffraction Grating Pattern

A polysilicon coated silicon wafer is immersed in a solution of a goat anti-(human IgG) antibody primary binding reagent of class IgG diluted in 0.1M phosphate buffered solution, pH 7.4, with 0.1 wt. % sodium azide preservative for 1 hr. The wafer is then removed from the antibody solution, rinsed with buffered saline, and dried.

A mask having a series of squares corresponding in size and shape to the ultimate chip product and with diffraction grating lines having a line spacing of 10 micrometers, a line width of 5 micrometers and a line density of 1000 lines/cm is clamped against the antibody coated surface of the polysilicon with a pressure of around 25 psi to minimize the spacing between the mask and chip surface. The mask surface is then exposed to ultraviolet light having a wavelength of 254 nm and a strength of 9.6 milliwatts per $cm^2$ for 3 min.

The wafer is then immersed in a 0.1M phosphate buffer solution (PBS), pH 7.4, containing 2.5 wt. % sucrose, 0.25 wt. % bovine serum albumin (BSA), and 0.1 wt. % sodium azide for 30 min, the excess is removed, and the wafer dried.

The wafer is then cut into square chips having a diffraction grating pattern of anti-IgE antibody thereon, and mounted in a receptive cavity on the surface of a dipstick.

EXAMPLE 2

Antigen Diffraction Grating Pattern

Repeating the procedure of Example 1, but replacing the anti-(human IgG) antibody with a ragweed pollen allergen, and exposing the mask to the ultraviolet light having a wavelength of 254 nm for 60 min yields a dipstick with chips on the surface thereof having a diffraction grating pattern of allergen thereon.

EXAMPLE 3

Serum IgG Immunoassay

The dipstick product of Example 1 is immersed in patient serum and incubated for 1 hr. The serum is removed, and the chip is rinsed three times with a buffered rinse solution containing 0.85 wt. % sodium chloride, 0.05 wt. % TWEEN 20 and 0.1 wt. % sodium azide preservative in a 0.01M aqueous phosphate buffer solution, pH 7.4. The diffraction grating pattern of anti-IgG antibody is conjugated with serum IgG.

The dipstick is then incubated 30 min with 100 microliters of a solution of goat anti-IgG antibody immobilized on 20 nm colloidal gold particles (E. Y. Laboratory, San Mateo, Calif.). The antibody is applied in a solution of 0.002M borate buffer, pH 8.5. The chip is rinsed thoroughly with distilled water.

The intensity of the light diffracted by the grating is then measured using polarized monochromatic light having a wavelength of 632.8 nm from a helium-neon laser.

The procedure is repeated with dilutions of human serum containing a known amount of IgG antibodies to establish a reference curve with which the intensity of the diffracted light obtained with the patient serum sample is compared.

EXAMPLE 4

Ragweed Specific IgE Immunoassay

A dipstick product of Example 2 having a diffraction grating pattern of ragweed pollen allergen thereon is contacted with patient serum to be assayed for ragweed pollen allergen binding IgE and incubated for 2 hrs. The serum is removed, and the chip is rinsed three times with a buffered rinse solution containing 0.85 wt. % sodium chloride, 0.05 wt. % TWEEN 20 and 0.1 wt. % sodium azide preservative in a 0.01 M aqueous phosphate buffer solution, pH 7.4. The diffraction grating pattern of ragweed pollen allergen is conjugated with serum IgE antibody.

The chip is then contacted for 30 min with 100 microliters of a solution of gold colloid particle labeled goat anti-IgE antibody (E.Y. laboratories, San Mateo, Calif.). The chip is rinsed thoroughly with distilled water.

The intensity of the light diffracted by the grating is then measured using polarized monochromatic light having a wavelength of 632.8 nm from a helium-neon laser.

The procedure is repeated with dilutions of human serum containing a known amount of ragweed pollen allergen specifically binding IgE antibodies to establish a reference curve with which the intensity of the diffracted light obtained with the patient serum sample is compared.

EXAMPLE 5

Serum IgG Immunoassay

The dipstick having a diffraction grating pattern of anti-(human IgG) antibody thereon prepared in accordance with the procedure of Example 2 is contacted with a mixture of 100 Microliters of patient serum and 100 1 microliters of a solution of gold colloid particle labeled goat anti-IgG antibody described in Example 3 and incubated for 1 hr. The chip is rinsed thoroughly with distilled water. The diffraction grating pattern of anti-IgG antibody is conjugated with serum IgG antibody conjugated with gold labeled anti-IgG antibody.

The intensity of the light diffracted by the grating is then measured using polarized monochromatic light having a wavelength of 632.8 nm from a helium-neon laser.

The procedure is repeated with dilutions of human serum containing a known amount of serum IgG antibodies to establish a reference curve with which the intensity of the diffracted light obtained with the patient serum sample is compared.

We claim:

1. A diffraction immunoassay plate for use in a light diffraction immunoassay comprising a surface selected from the group consisting of polysilicon and crystalline silicon surfaces having on said surface, a biological diffraction grating design of lines of active binding reagent.

2. The diffraction immunoassay plate of claim 1 wherein the diffraction binding assay surface is polysilicon.

3. The diffraction immunoassay plate of claim 1 wherein the active binding reagent is proteinaceous.

4. The diffraction immunoassay plate of claim 1 wherein the binding reagent is selected from the group consisting of antibody, antigen, hapten, protein A, lectin, biotin and avidin.

5. The diffraction immunoassay plate of claim 1 wherein the biological diffraction grating design of lines of active binding reagent is non-light disturbing.

6. A diffraction binding assay method for determining the presence or quantity of an analyte in an aqueous sample comprising
    (a) contacting a diffraction binding assay surface with the sample for time sufficient to permit conjugation of binding reagent and analyte, the diffraction binding assay surface being selected from the group consisting of polysilicon and single crystalline silicon surfaces having on said surface, a light disturbing design of substantially non-light disturbing binding reagent thereon, the binding reagent being selected to bind selectively with the analyte;
    (b) separating the surface from the sample; and
    (c) illuminating the diffraction binding assay surface with light from a light source, and determining the light diffraction by the diffraction binding assay surface.

7. The diffraction binding assay method of claim 6 wherein the diffraction binding assay surface is polysilicon.

8. The diffraction binding assay method of claim 6 wherein the smooth insoluble surface has been treated with an aqueous solution of a non-specific binding inhibitor.

9. The diffraction binding assay method of claim 6 wherein the non-specific binding inhibitor is a water-soluble protein or polyamino acid.

* * * * *